US 6,684,428 B2

(12) United States Patent
Grotenhuis et al.

(10) Patent No.: US 6,684,428 B2
(45) Date of Patent: Feb. 3, 2004

(54) HEAD-CLAMPING DEVICE FOR SURGICAL PURPOSES

(75) Inventors: J. André Grotenhuis, Nijmegen (NL); Theo J. J. Zegers, Ledeacker (NL); Kurt Dieter Von Zeppelin, Pullach (NL)

(73) Assignees: Theo J.J Zegers, Ledeacker (NL); Kurt Dieter Von Zeppelin, Pullach (DE)

(*) Notice: Subject to any disclaimer, the term of this patent is extended or adjusted under 35 U.S.C. 154(b) by 27 days.

(21) Appl. No.: 09/797,730

(22) Filed: Mar. 5, 2001

(65) Prior Publication Data

US 2001/0029379 A1 Oct. 11, 2001

(30) Foreign Application Priority Data

Mar. 3, 2000 (DE) .......................................... 100 10 384

(51) Int. Cl.⁷ ................................................ A61G 13/12
(52) U.S. Cl. .................................... 5/637; 5/622; 5/640
(58) Field of Search ............................ 5/622, 621, 637, 5/636; 128/857

(56) References Cited

U.S. PATENT DOCUMENTS

| 3,099,441 A | * | 7/1963 | Rles ................................ 5/637 |
| 3,853,861 A | * | 12/1974 | Garbrecht .................... 540/218 |
| 4,108,426 A | * | 8/1978 | Lindstroem et al. ........... 5/637 |
| 4,169,478 A |   | 10/1979 | Hickman |
| 5,269,034 A | * | 12/1993 | Day et al. ........................ 5/622 |
| 5,276,927 A | * | 1/1994 | Day ................................ 5/622 |
| 5,537,704 A | * | 7/1996 | Dinkler .......................... 5/622 |
| 6,381,783 B2 | * | 5/2002 | Reinhardt et al. .............. 5/622 |

FOREIGN PATENT DOCUMENTS

| DE | PS86665 | 6/1895 | |
| DE | UM7524814 | 8/1975 | |
| DE | 2809645 | 11/1978 | ........... A61B/17/02 |
| DE | 1984347 | 6/1999 | ........... A61B/17/60 |
| EP | 0938873 | 9/1999 | ........... A61B/19/00 |

* cited by examiner

Primary Examiner—Heather Shackelford
Assistant Examiner—Frederick Lyndon Lagman
(74) Attorney, Agent, or Firm—Mark M. Friedman (57) ABSTRACT

The present invention relates to a head-clamping device for surgical purposes, specifically for intra-operatively fixing the patient's head in any anatomically possible position, the center of rotation of the head clamp being in the cervical vertebral region of the patient.

31 Claims, 12 Drawing Sheets

Max. 170°

Fig. 10A FLEXION AND EXTENSION (YES MOVEMENT)

Fig. 10B LATERAL TILT (SIDEWAYS)

Fig. 10C SIDE-TO-SIDE MOVEMENT (NO MOVEMENT)

Fig. 10D The point of intersection of the vertical and horizontal median lines denotes the head joint.

HEAD-CLAMPING DEVICE FOR SURGICAL PURPOSES

FIELD OF THE INVENTION

The present invention relates to a head-clamping device for surgical purposes, specifically for intra-operatively fixing the patient's head in any anatomically possible position, the center of rotation of the head clamp being in the cervical vertebral region of the patient.

BACKGROUND OF THE INVENTION

Precise operations on the brain, particularly in neurosurgery, require that the head of the anesthetized patient should not move. This is achieved by a head-clamping device attached to the operating table.

A head clamp in which the head is clamped between three steel arbors is known from U.S. Pat. No. 3,099,441. The points of these arbors are pressed into the skull by an adjustable force. The arbors are arranged on two diametrically opposed arms. One arm is provided with an axially adjustable clamp for one arbor and the other arm is provided with a clamp with two arbors which is also axially adjustable but is centrally pivoting.

These head clamps have proved their worth in practice for decades to fix the head in the desired, anatomically exact position. It is, however, extremely difficult and troublesome to change the position of the head with the known head clamps during the operation. But such a position change becomes increasingly necessary in minimally invasive operations to make the surgical region accessible and visible.

It is another disadvantage that the design requires the division of the known number of three arbors into 1+2 and that additionally the two arbors which are arranged together in a common, usually rotating clamp are not axially adjustable, i.e. neither the distance between the two points nor their angle of inclination can be adjusted. It is another disadvantage that particular bulky components of the head clamp are placed under the head of the lying patient and thus interfere with the legs of the sitting surgeon or of an assistant joining him from the side.

With the strongly increasing endoscopy in neurosurgery, the intra-operative position change has gained further importance. For operations using an endoscope, a much smaller opening in the skull is sufficient, facilitating the postoperative restoration of a patient's health. In endoscopic and endoscope-aided microneurosurgical operations, it is extremely essential to be able to slightly change the position of the clamped head during the operation. This should be possible in a simple, rapid, stepless and ergonomic way.

A device for head surgeries comprising a spreading device is known from DE 28 09 645 A1. A head clamp allowing a simple fixation of the head is known from DE-PS 86665.

A clamping joint for medical devices and apparatuses which can also be used for head clamps is known from DE 198 54 347 A1.

A clamping device for medical instruments which comprises a flexible link arm is described in DE-UM 75 24 814. A surgical head clamp comprising a frame is known from U.S. Pat. No. 4,169,478. EP 0 938 873 A2 describes a stereotactic positioning device for a patient to be irradiated.

SUMMARY OF THE INVENTION

FIGS. 10A–10D illustrate the different movement directions of the head at the upper end of the human vertebral column.

Figure 10A:
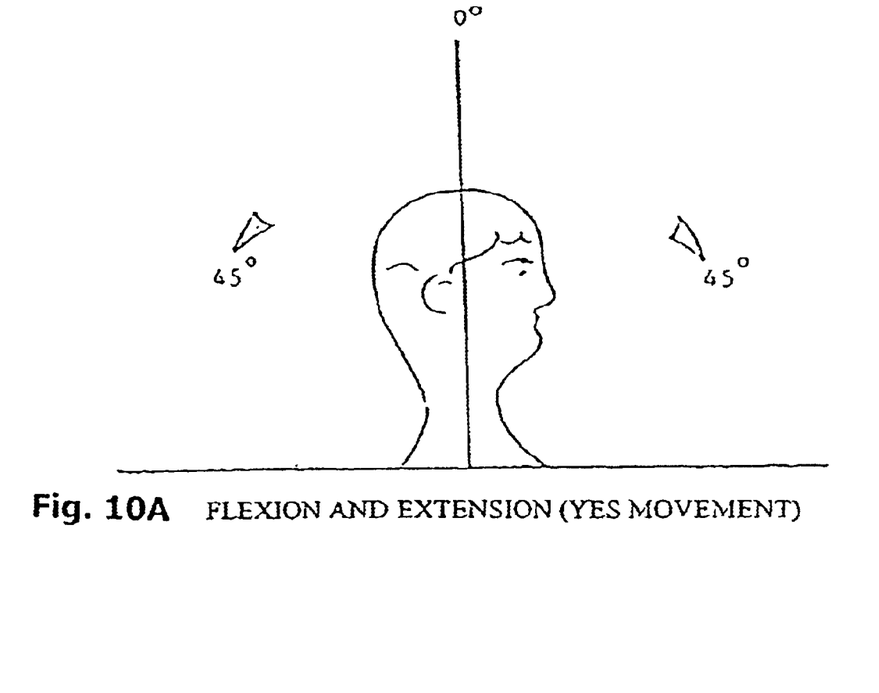
FIGS. 10A–10D illustrate the different movement directions of the head at the upper end of the human vertebral column.
Figure 10B:
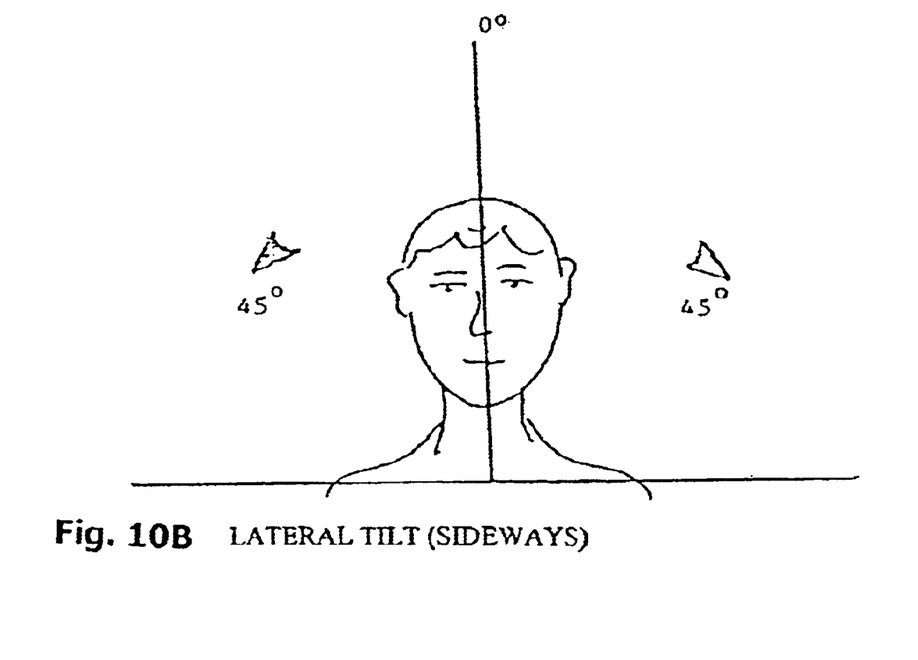

FIG. 10A shows the flexion and extension (YES movement) of the head in which the head is inclined vertically to the front and back. FIG. 10B shows the transverse inclination or lateral tilt of the head to the left and right.

Figure 10C:
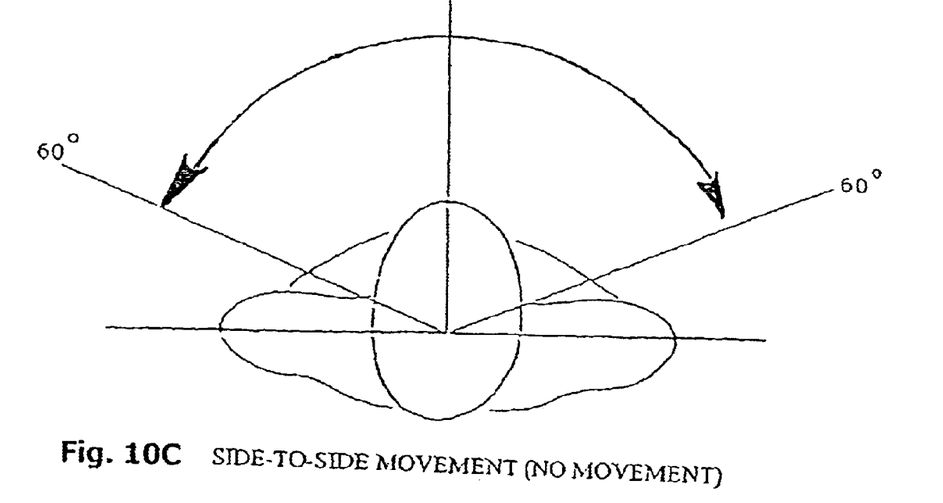

FIG. 10C shows the side-to-side movement of the head (NO movement).

Figure 10D:
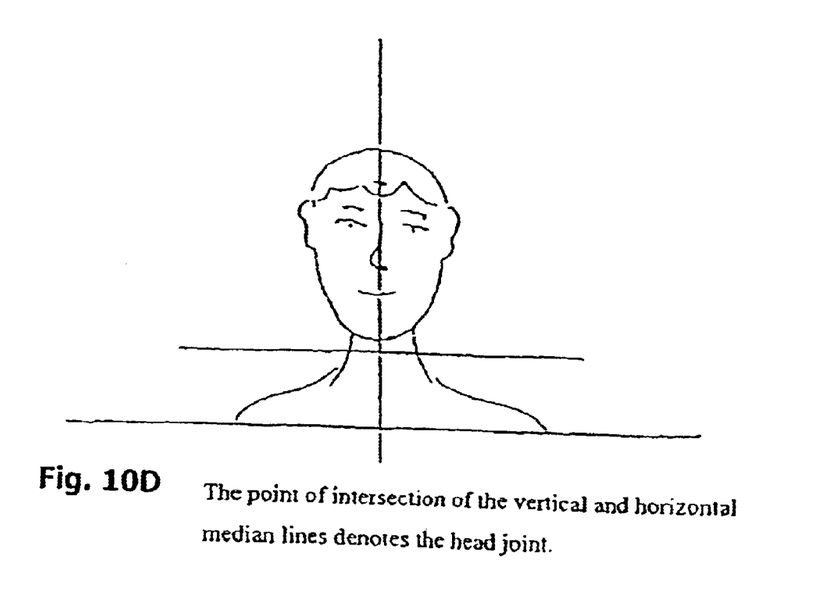

FIG. 10D shows the point of intersection of the vertical and horizontal median lines in the head joint.

It appears from FIGS. 10A–10D that a head clamp adjusted to the anatomical conditions should take account of the three degrees of freedom shown in FIGS. 10A–10C, whereas according to FIG. 10D the center of rotation of the head clamp should be in the cervical vertebral region of the patient, i.e. near the two upper vertebrae (atlas and epistropheus).

Therefore, an efficient head clamp to be used in neuroendoscopy and endoscope-aided microneurosurgery should meet the following requirements. It should be possible to clamp the head in any anatomically possible initial position and to move it by means of the head clamp in the three directions illustrated in FIGS. 10A–10C. It should be possible to perform these movements simply and without any operative trouble. These movements should be steplessly variable and rapidly fixable in any position. The center of rotation of the three movements should be in the two upper cervical vertebrae. Moreover, the center of rotation of the head clamp should be also on the median lines of said cervical vertebrae of the patient. The space below the head of the lying patient should be free of hindering mechanisms.

It is, therefore, the problem of the invention to provide a head-clamping device for surgical purposes which meets the above-mentioned requirements and, in addition, allows a division of the at least two arbors into 1+1, i.e. allows at least two clamps with one arbor each, the two or even three clamps being steplessly adjustable to each other in such a way that the point of intersection of the extended lines of the three arbors is always on the vertical median line of the upper cervical vertebrae.

This problem is solved according to the invention by a head-clamping device according to claim 1. The frame can be pivoted on an axis (x) which represents the tilting movement sideways which is shown in FIG. 10B. The profile pivoting on an axis (y) allows the flexion and extension of the head (YES movement) shown in FIG. 10A. Finally, the mating profile pivoting on an axis (z) allows the side-to-side movement (NO movement) of the head shown in FIG. 10C.

It is preferred that the profile and the mating profile are curved in the shape of a circular segment throughout. This prevents the central point from shifting when the mating profile is pivoted on the profile.

Preferably, a headrest is attachable to the mating profile. This allows an additional supporting of the head if two clamping arbors are used.

The head clamps can be attached to the mating profile in any position. This allows the free adjustment and re-arresting of the clamp points.

The pivoting movements on the axes (x, y, z) can be performed steplessly and can be fixed in any position or they have a self-locking design. This allows the universal use and easy repositioning of the head-clamping device.

Preferably, the axes (x, y, z) are perpendicular to each other so that any position of the head can be adjusted with three independent degrees of freedom within the limits of the head inclination angle.

BRIEF DESCRIPTION OF THE DRAWINGS

Other advantages, features, and applications of the present invention will appear from the following description of an embodiment in conjunction with the drawings, in which.

DETAILED DESCRIPTION OF THE PREFERRED EMBODIMENT

Figure 1:
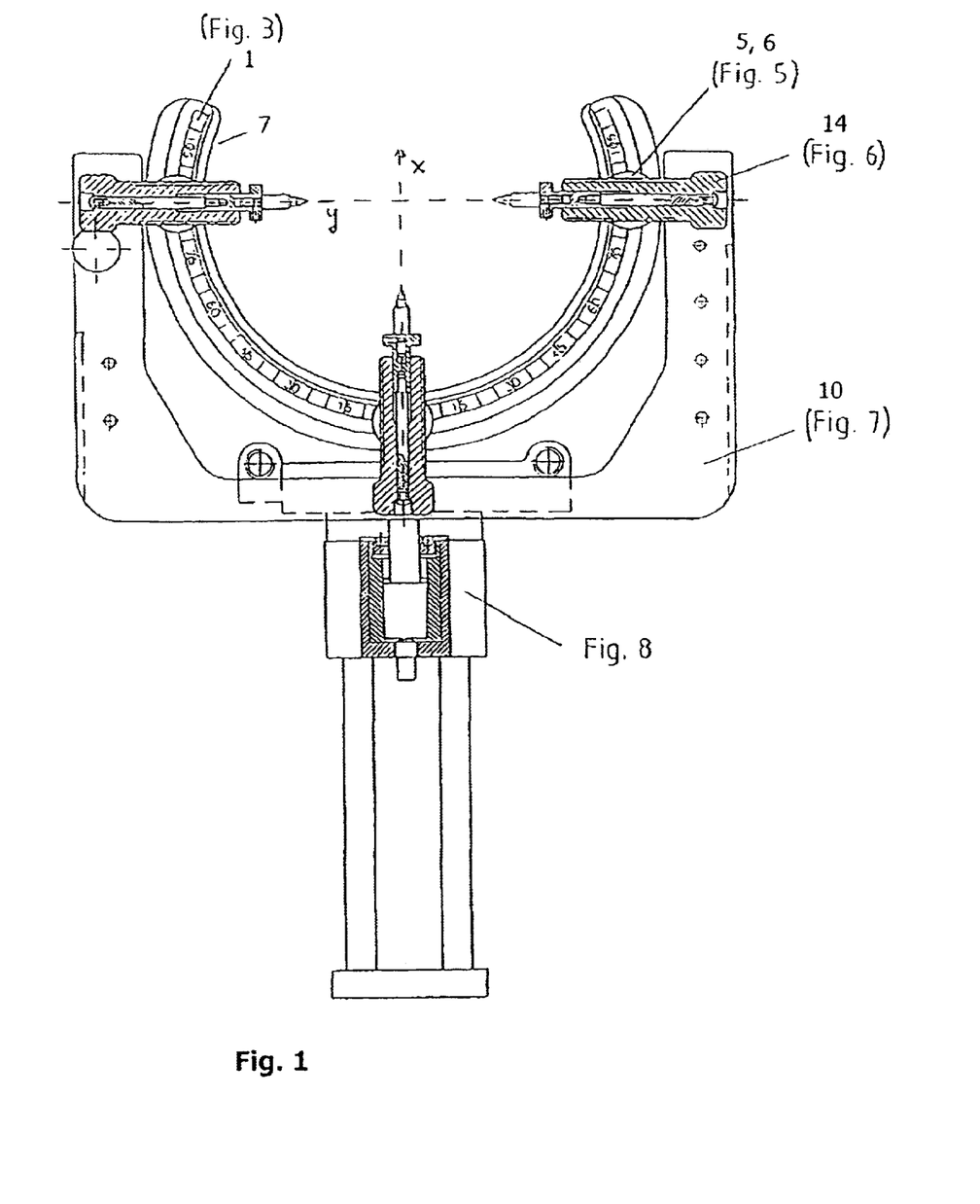
FIG. 1 shows the front view of an embodiment of the head-clamping device according to the invention.
Figure 2:
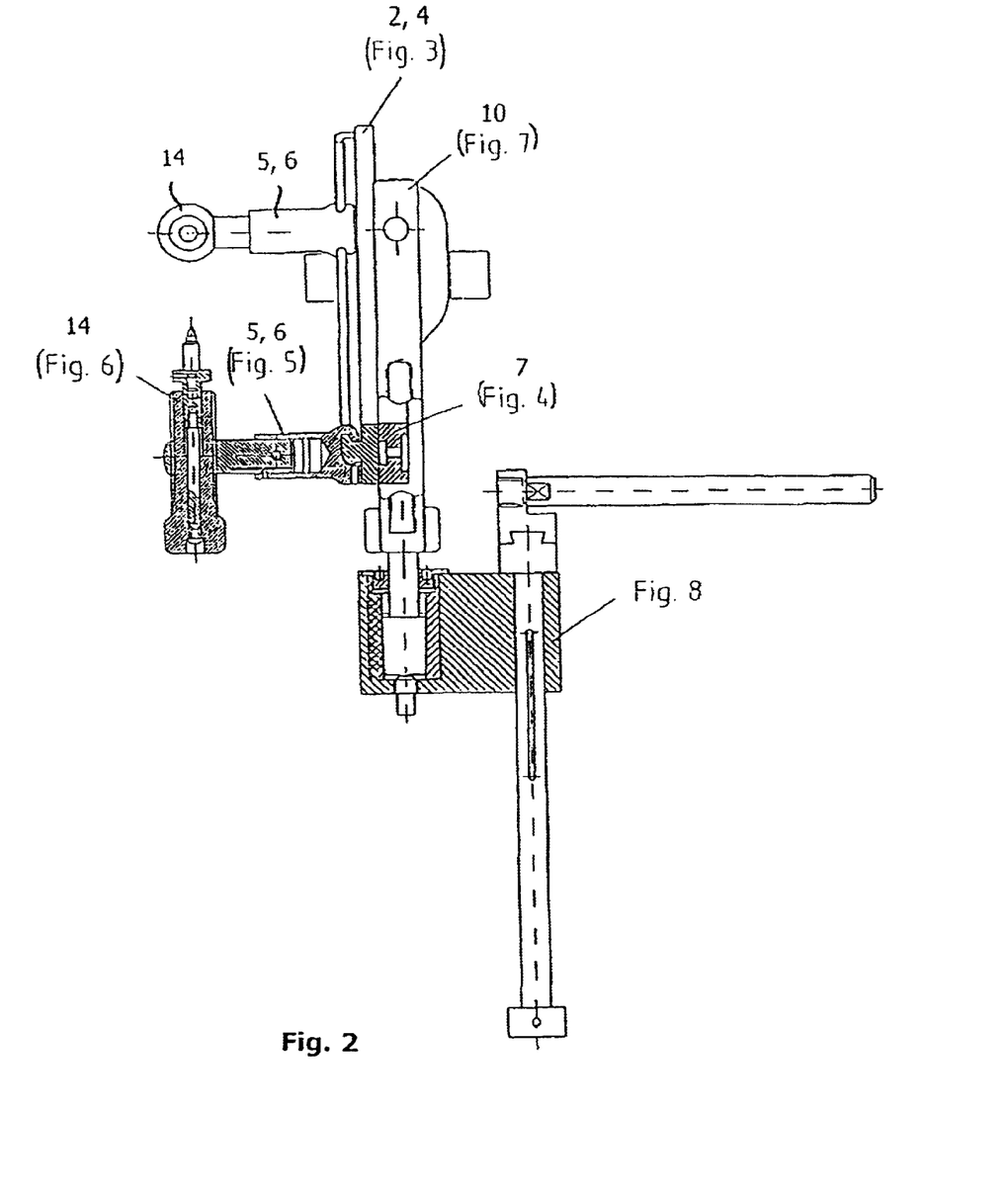
FIG. 2 shows the side view of the embodiment of the head-clamping device according to the invention.

FIGS. 1 and 2 clearly show the front and side views of all elements of the head-clamping device according to the invention. A frame 10 provided with two legs facing each other as illustrated in FIG. 7 is pivoted on an axis (x) and is attached to an operating table as shown in FIG. 8. A profile 7 pivoting on an axis (y) is attached to the frame 10, i.e. between the legs facing each other, the profile 7 acting together with the mating profile 1 as illustrated in FIG. 3 to be pivoting on an axis (z). Two head clamps 5, 6 carrying one clamping arbor 14 each are attached to the mating profile 1 so that they face each other. Another head clamp is attached to the lowest possible position of the mating profile 1.

Figure 3A:
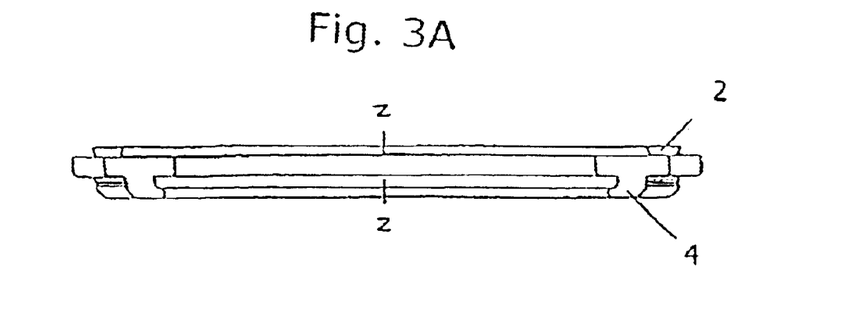
FIGS. 3A, 3B and 3C, respectively, show the side, top and cross-sectional views of the mating profile for use with the head-clamping device according to the invention.
Figure 3B:
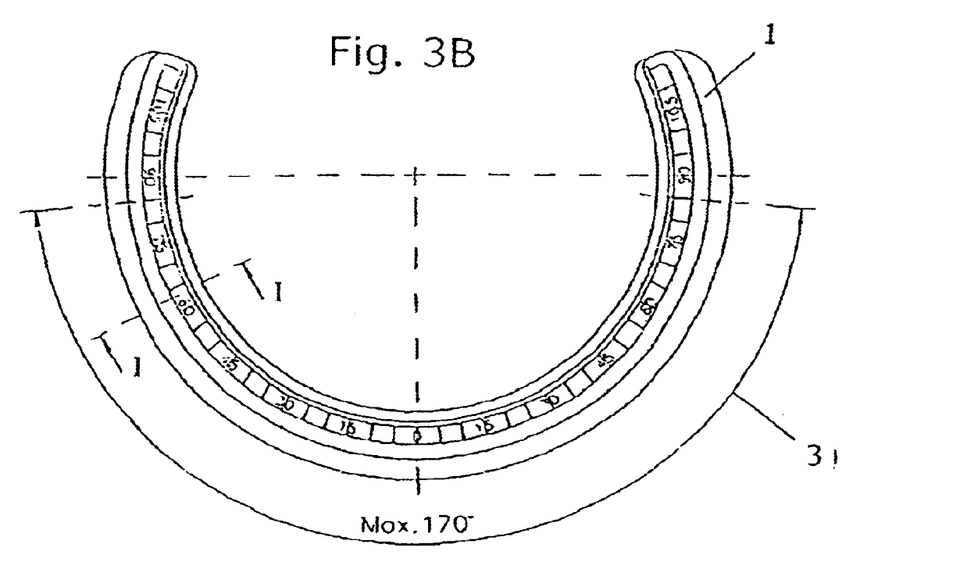
Figure 3C:
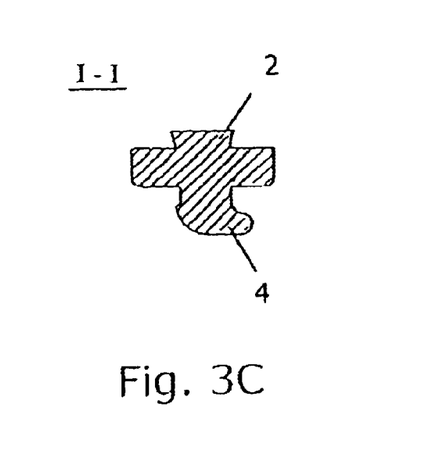
Figure 4A:
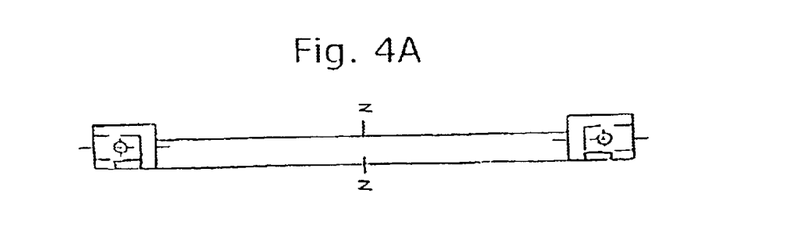
FIGS. 4A, 4B, 4C and 4D, respectively, show the side, top, front and cross-sectional views of a profile for use in head-clamping device according to the invention.
Figure 4B:
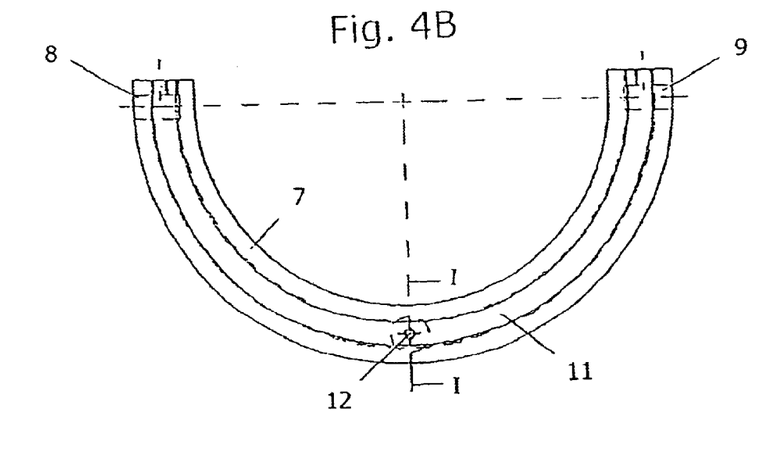
Figure 4C:
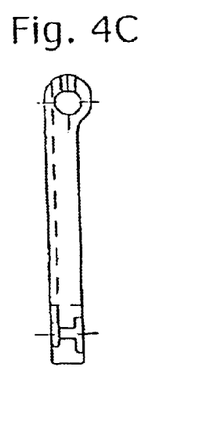
Figure 4D:
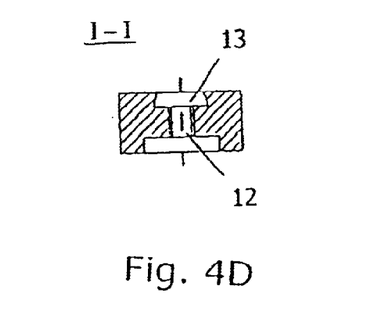
Figure 5A:
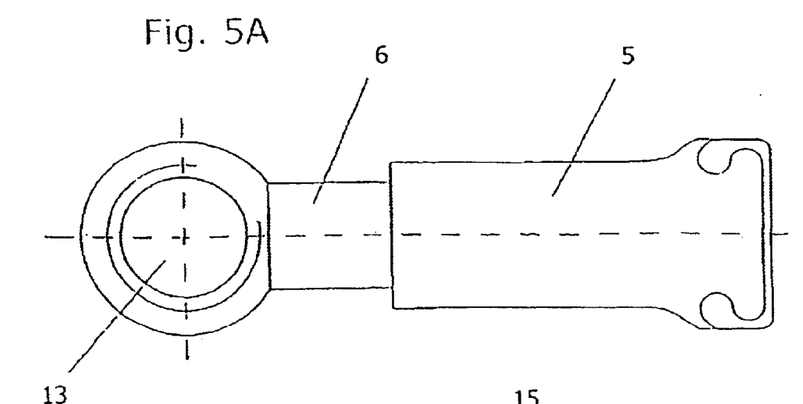
FIGS. 5A, 5B, 5C and 5D show several views of the head clamp for use with the head-clamping device according to the invention.
Figure 5B:
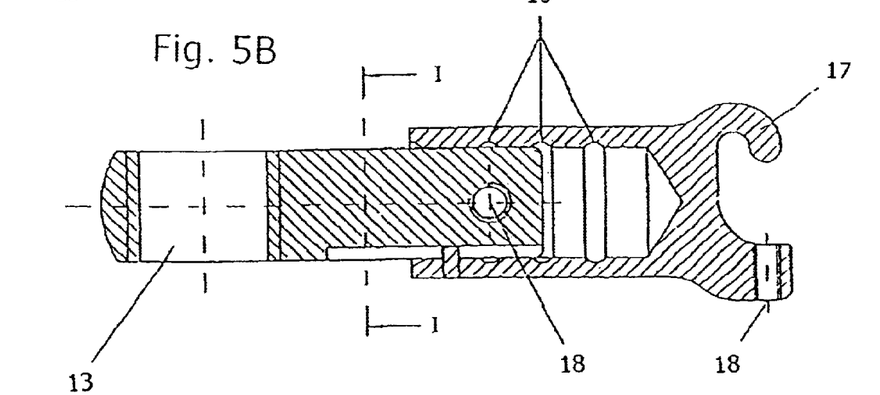
Figure 5C:
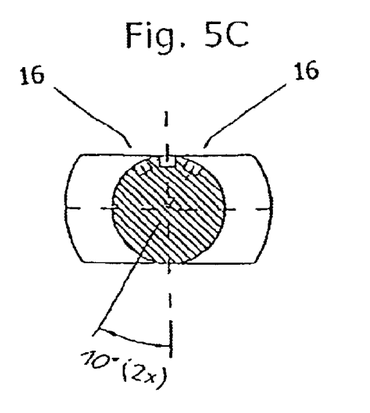
Figure 5D:
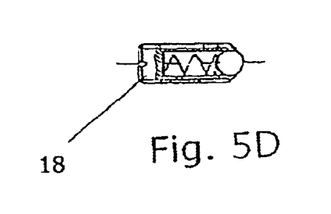

FIG. 3 shows the pivoting, profiled and graduated mating profile 1 having the shape of a circular segment which is designed for the NO movement (side-to-side movement). The back profile part 2 in the cross-sectional view is the male part of a dovetail guide having a circular-segment-shaped radian measure 3 of 170°. The back profile part 2 is therefore intended as an engaging member in the profile 7 shown in FIG. 4. The front profile part 4 is provided with a shoulder shown in the cross-sectional view and is intended for engaging the axially adjustable two-part head clamps 5, 6, 14 as they are shown in FIG. 5. Therefore, the back profile part 2 is a protruding dovetailed engaging part, whereas the front profile part 4 is a protruding part provided with a shoulder.

FIG. 4 shows the side, front, top and cross-sectional views of a profiled circular-segment-shaped profile 7 for the YES movement (flexion, extension). The profile 7 has two recesses or holes 8, 9 used for pivoting it in the frame 10 (FIG. 7) on two axle shafts. The profile 7 has a back part and a front part 11 which is the female part of a dovetail guide which is intended for the engagement of the profile part 2 of the mating profile 1. In a tapped hole 12, the mating profile 1 can be non-positively fixed with a commercial clamping screw in the profile 7.

Figure 6:
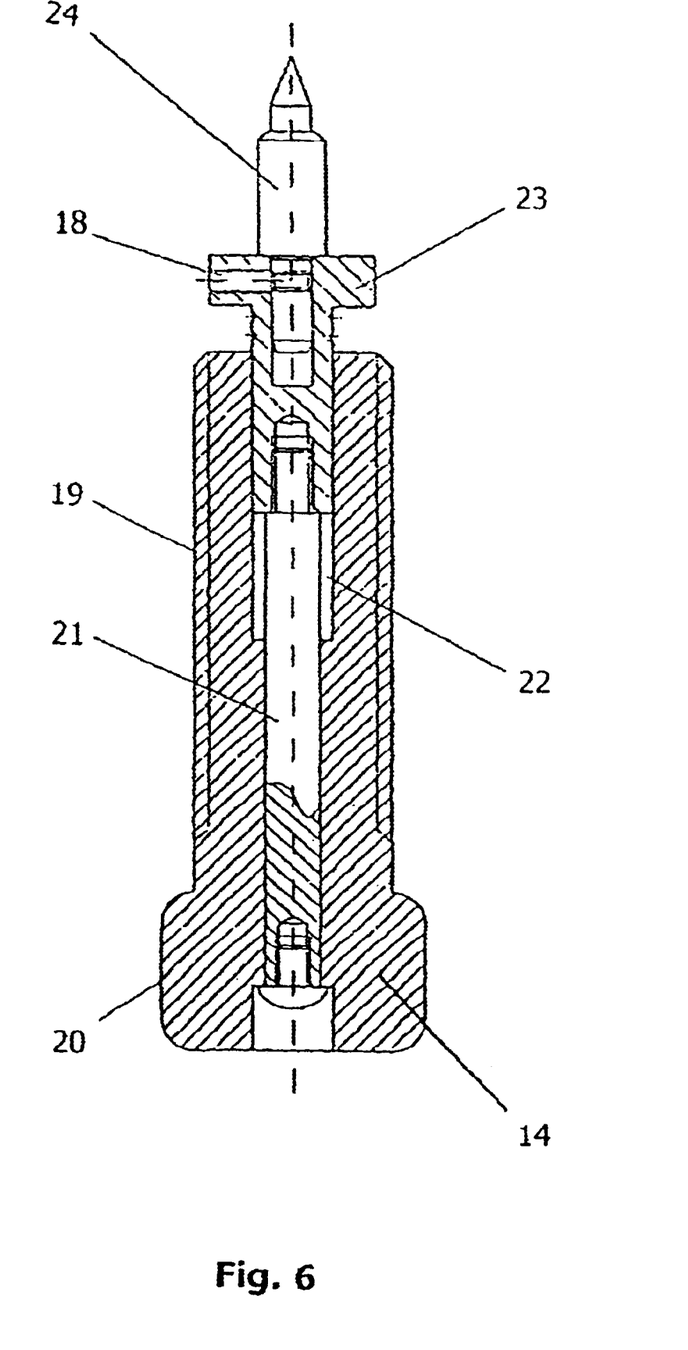
FIG. 6 shows a clamping arbor for use in the head-clamping device according to the invention.

FIG. 5 shows several views of an axially adjustable two-part head clamp 5, 6. A tapped hole 13 is used for receiving a radially adjustable clamping arbor 14 (FIG. 6). The clamping arbor 14 can be axially positioned in three different positions, namely −90° and 10° to the left and right. In any possible position, the head clamp can be fixed by means of a commercial springable thrust piece 18 by engaging it. The front part 5 of the head clamp is shaped like a cam in the front at 17 in such a way that it can be engaged in the front part 4 of the mating profile 1 (NO movement) using a commercial springable thrust piece 18. In addition, the attaching by engaging the head clamp 5, 6 in the profile part 4 allows the head clamp to be moved in both directions and thus allows a variable position of the head clamp in the mating profile.

FIG. 6 shows the cross-sectional view of a clamping arbor 14 which can be adjusted radially. The clamping arbor 14 consists of a screw 19 with a lathe-turned handwheel 20. This combination is provided with a hole for receiving a bar 21, a pressure spring 22, an arbor receptacle 23, and an arbor 24. The arbor 24 is retained in the receptacle 23 by means of a commercial springable thrust piece 18.

Figure 6A:
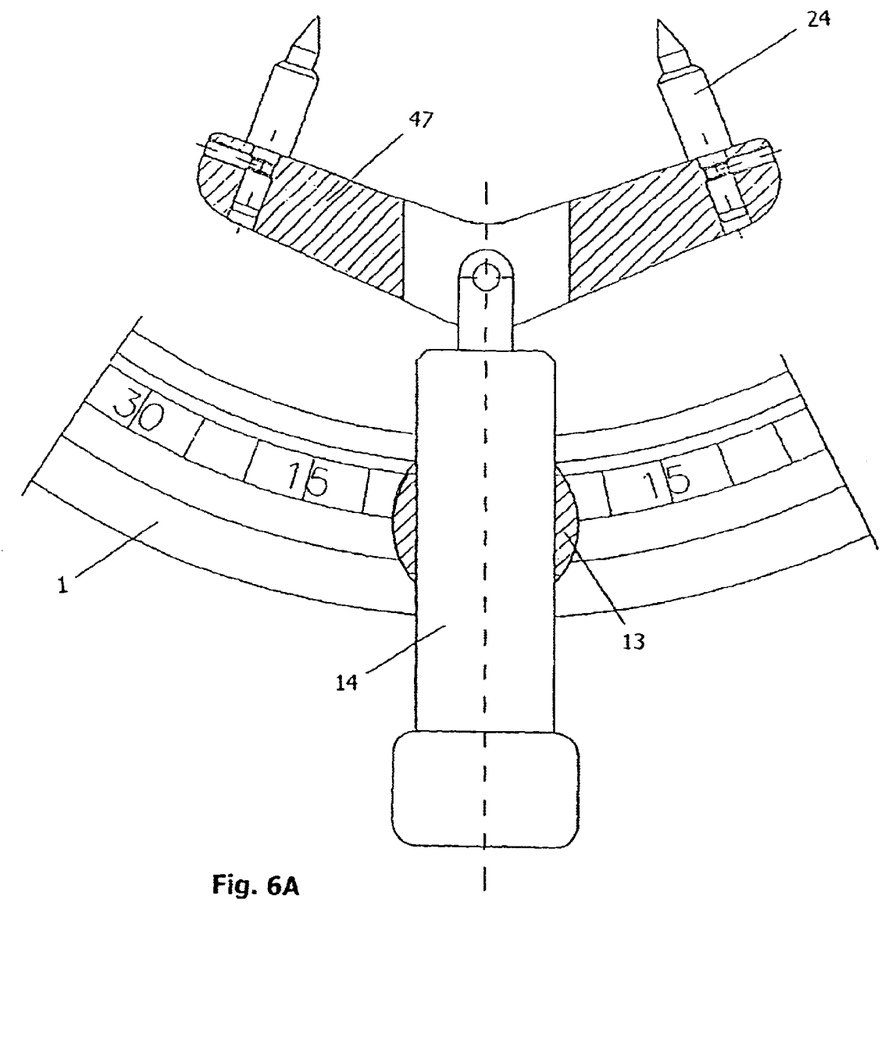
FIG. 6a shows an alternative embodiment of a head clamp for use in the head-clamping device according to the invention.

FIG. 6a shows an embodiment of the head clamp with two arbors. Two arbors 24 are preferably symmetrically arranged in positions in which they face each other and are attached in a common clamp 47 which is both rotating and pivoting. This alternative clamping arbor can also be screwed into the tapped hole 13 of the axially adjustable head clamp 5, 6 and can thus be engaged in the front part 4 of the mating profile 1 for the NO movement. Therefore, the alternative head clamp can be engaged in the same way of attachment as is described with reference to FIG. 5.

Figures 7A, 7C, 7D:
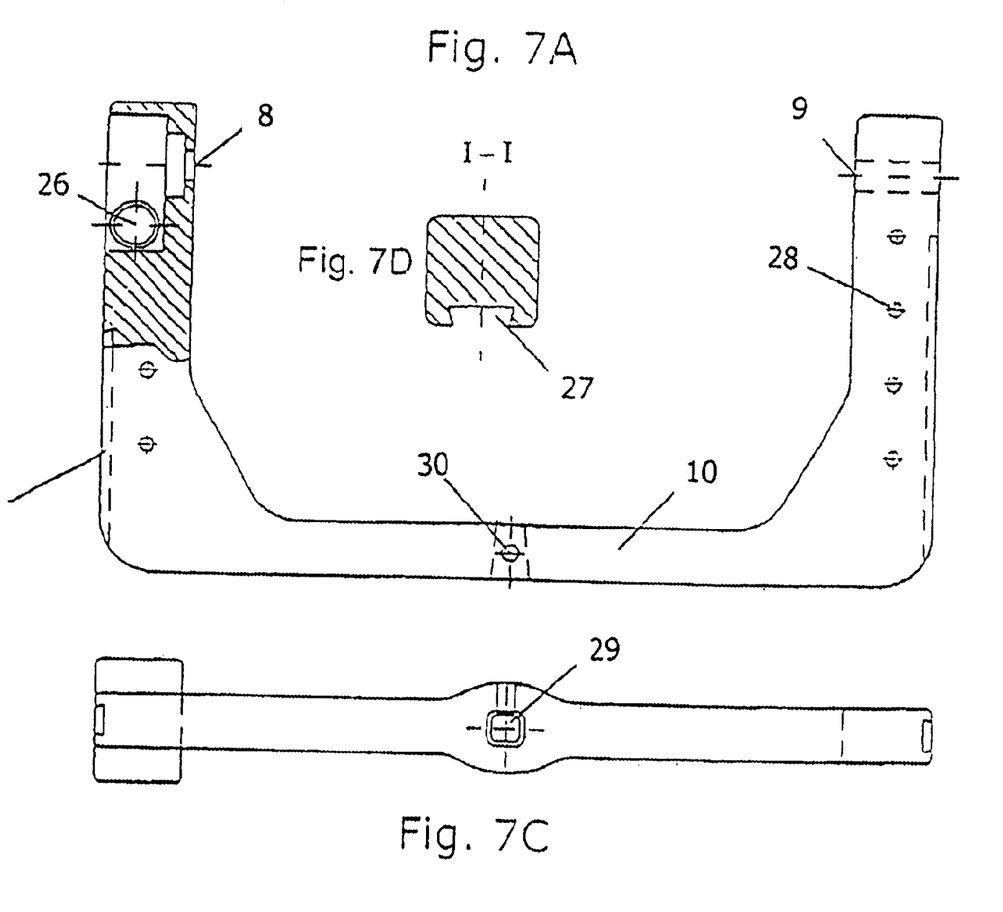
FIGS. 7A, 7B, 7C and 7D, respectively, top, side, bottom and cross-sectional views of the frame for use in the head-clamping device according to the invention.
Figure 7B:
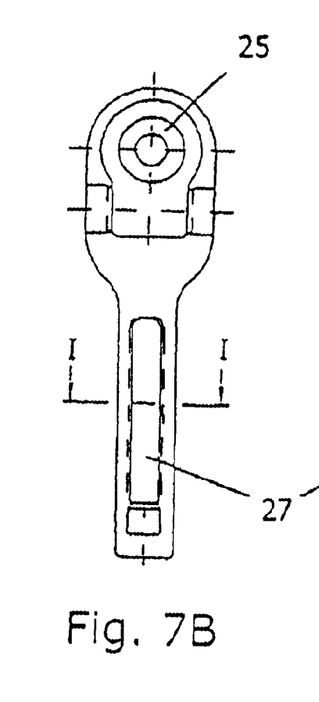
Figure 8:
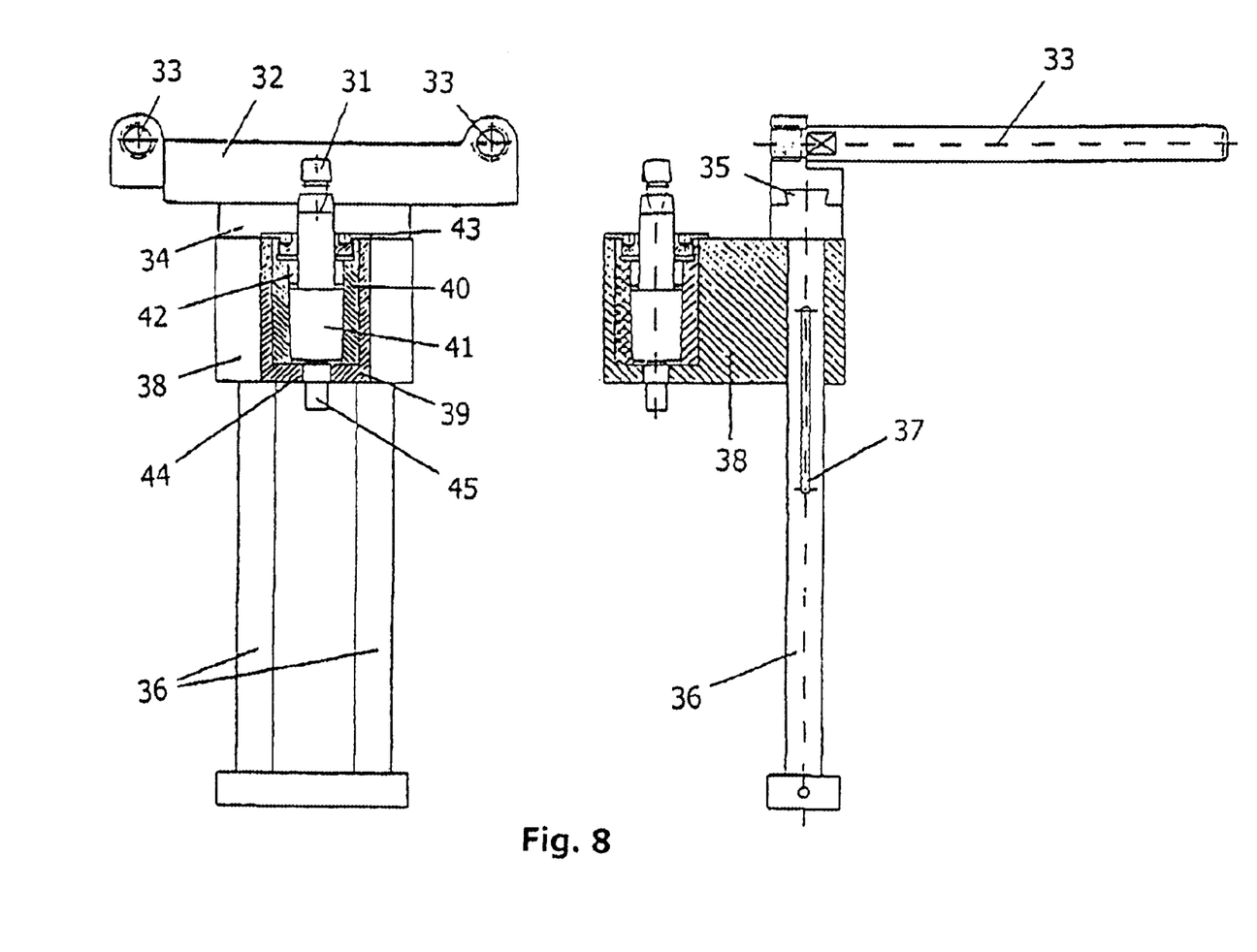
FIG. 8 shows the front and side views of the attachment of the head-clamping device according to the invention to an operating table.

FIG. 7 shows the top, side, bottom and cross-sectional views of a frame 10. The two legs facing each other are clearly visible. Holes 8, 9 are formed for receiving the profile 7 (FIG. 4). The profile 7 is pivoted by means of two shafts in the holes 8, 9 in the frame and is moved by means of a worm-gear set 25 with a turning knob 26. The self-locking device of the worm-gear set 25 effects a non-positive fixation of the profile 7 in any position. The two faces of the legs of the frame 10 are provided with the female part of a dovetail guide 27 and a number of holes 28. Both the dovetail guide 27 and the holes 28 are used for the attachment of auxiliary equipment for the operation. Using a conical square hole 29 in the horizontal bar of the frame 10 which connects the two legs, the frame 10 is pushed onto an external carrier such as an attaching device 31 (FIG. 8) and is locked in a tapped hole 30 by means of a commercial springable locking bolt.

FIG. 8 shows how the head-clamping device according to the invention is mounted to an attaching device 31 of an operating table. This device consists of a radially adjustable two-part rail 32 with two fixing bars 33 for insertion into the pipes with which every neurosurgical operating table is equipped and a second rail 34 which is movably arranged in a dovetail guide 35 of the first rail 32 and is provided with two holes for receiving two guide bars 36. The two rails 32, 34 are fixed by means of a commercial clamping screw in the central tapped hole.

One of the two guide bars 36 is provided with a large number of holes 37 arranged side by side in such a way that the next hole intersects the preceding one. Using this side-by-side arrangement of holes, the whole frame 10 can be fixed with a commercial locking bolt.

The carrier 38 slides on the guide bars 36 of the frame 10. This carrier 38 consists of a case 39, a bush with taper socket 40, a shaft with cone shaft 41 and conical square, a pressure spring 42, and a cap 43. The case bottom has a tapped hole 44 for receiving a threaded bolt 45 provided with a commercial clamping sleeve with handle. By turning the clamping sleeve by means of the handle, the bolt moves upwards by a part of its thread pitch and releases the self-locking device of the cone. This allows the turning of the frame 10 and the adjustment of the lateral inclination of the patient's head.

Figure 9:
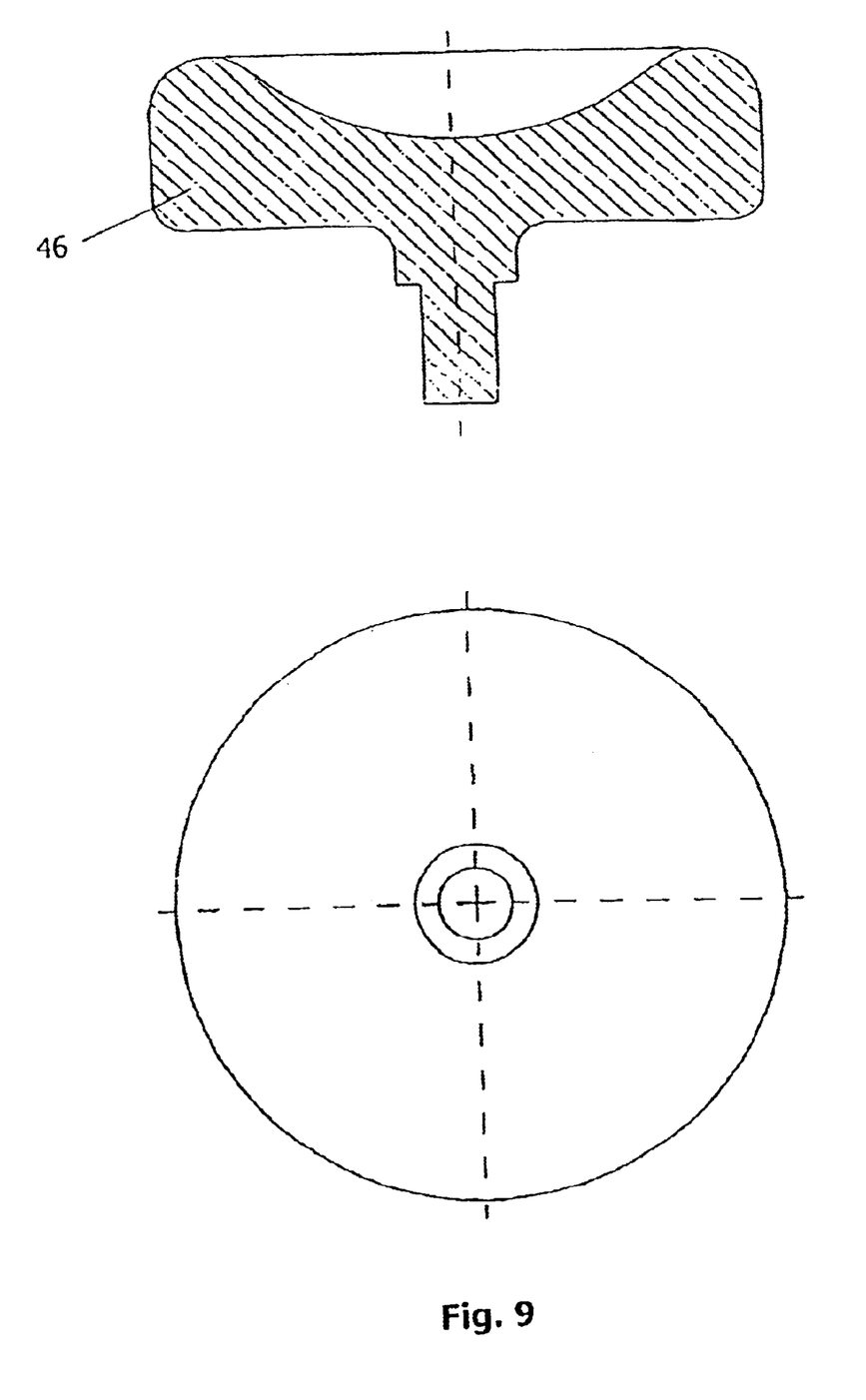
FIG. 9 shows the sectional and top views of a headrest for use in the head-clamping device according to the invention.

FIG. 9 shows the sectional and top views of a headrest 46 which is adapted to the shape of the skull. This headrest can be inserted into a head clamp with lathe-turned handwheel 19, 20 and facilitates the clamping of the head by means of the arbors 24. In addition, the headrest 46 allows X-rays to be taken intra-operatively because the non-radiolucent head clamp with the arbors can be removed by simply disengaging it and can be re-attached after the X-rays have been taken.

The invention provides therefore a head-clamping device for clamping and fixing the head of a patient, in particular for neurosurgical operations, in which the head can be clamped and fixed in any anatomically possible position from which the head can be moved by means of the clamp in three directions, namely, in a forward and backward, laterally inclined and side-to-side direction.

A special feature of the head clamp according to the invention is that for each of the above-mentioned movements the center of rotation of the clamp is on the median line of the patient's cervical vertebrae. The above-mentioned movements can be steplessly adjusted by means of the head-clamping device according to the invention and can be fixed in any position by means of an arresting device or are self-locking.

In the head-clamping device according to the invention, the clamps provided with arbors rest in a preferably two-part circular segment which is pivoted in the frame by means of two laterally attached shafts and is either fixable or self-locking to allow the YES movement of the head.

In the head clamp according to the invention, the circular segments rested in each other can be turned towards each other and can be fixed to allow a NO movement (side-to-side movement) of the head.

In the head-clamping device according to the invention, the front part of the circular segment for the NO movement (side-to-side movement) is profiled in such a way that the axially adjustable head clamps with the screwed-in, radially adjustable clamping arbors can be engaged in any position and can be moved from there in both directions.

The circular segment for the NO movement (side-to-side movement) is uniformly graduated from the lower zero point in both directions to ensure a positioning to the degree.

In the head-clamping device according to the invention, the frame attached to the attachment part of the operating table can be pivoted and can be fixed in any position to allow the lateral tilting movement (FIG. 10B) of the head. The frame attached to the attachment part of the operating table can be vertically adjusted almost steplessly and can preferably be fixed with a commercial locking bolt in any position of the adjusting range.

Using the radially and axially adjustable head clamp, both the arbor and a headrest adapted to the shape of the skull can be inserted, namely by the same way of attachment using a commercial springable thrust piece.

The head-clamping device according to the invention can be used by means of the above-mentioned attachment devices in surgeries in both a lying and a sitting patient and provides therefore a versatile head clamp adaptable to different conditions.

We claim:

1. A head-clamping device for surgical purposes comprising a frame (10) attachable to an external carrier which can be pivoted around an axis (x), the frame comprising legs facing each other;

a profile (7) which is arranged between the legs and is supported pivotably on an axis (y), the profile (7) being uniformly curved at least in sections and comprising a rail (11) in the curved section;

a mating profile (1) which is supported in the rail (11) of the profile (7), the mating profile (1) being pivotable around an axis (z) when it is moved; and at least two head clamps (5, 6, 14) attachable to the mating profile (1) which comprise clamping arbors (14) between which the head is clamped and fixed.

2. The head-clamping device as claimed in claim 1 in which the profile (7) and the mating profile (1) are curved throughout in the shape of a circular segment.

3. The head-clamping device as claimed in claim 1 in which a headrest (46) can be attached to the mating profile (1).

4. The head-clamping device as claimed in claim 2 in which a headrest (46) can be attached to the mating profile (1).

5. The head-clamping device as claimed in claim 1 in which the head clamps (5, 6, 14) can be attached in any position to the mating profile (1).

6. The head-clamping device as claimed in claim 2 in which the head clamps (5, 6, 14) can be attached in any position to the mating profile (1).

7. The head-clamping device as claimed in claim 3 in which the head clamps (5, 6, 14) can be attached in any position to the mating profile (1).

8. The head-clamping device as claimed in claim 4 in which the head clamps (5, 6, 14) can be attached in any position to the mating profile (1).

9. The head-clamping device as claimed in claim 1 in which the pivoting movements around the axes (x, y, z) can be performed continuously and can be fixed in any position or are self-locking.

10. The head-clamping device as claimed in claim 2 in which the pivoting movements around the axes (x, y, z) can be performed continuously and can be fixed in any position or are self-locking.

11. The head-clamping device as claimed in claim 3 in which the pivoting movements around the axes (x, y, z) can be performed continuously and can be fixed in any position or are self-locking.

12. The head-clamping device as claimed in claim 4 in which the pivoting movements around the axes (x, y, z) can be performed continuously and can be fixed in any position or are self-locking.

13. The head-clamping device as claimed in claim 5 in which the pivoting movements around the axes (x, y, z) can be performed continuously and can be fixed in any position or are self-locking.

14. The head-clamping device as claimed in claim 6 in which the pivoting movements around the axes (x, y, z) can be performed continuously and can be fixed in any position or are self-locking.

15. The head-clamping device as claimed in claim 7 in which the pivoting movements around the axes (x, y, z) can be performed continuously and can be fixed in any position or are self-locking.

16. The head-clamping device as claimed in claim 8 in which the pivoting movements around the axes (x, y, z) can be performed continuously and can be fixed in any position or are self-locking.

17. The head-clamping device as claimed in claim 2 in which the axes (x, y, z) are perpendicular to each other.

18. The head-clamping device as claimed in claim 3 in which the axes (x, y, z) are perpendicular to each other.

19. The head-clamping device as claimed in claim 4 in which the axes (x, y, z) are perpendicular to each other.

20. The head-clamping device as claimed in claim 5 in which the axes (x, y, z) are perpendicular to each other.

21. The head-clamping device as claimed in claim 6 in which the axes (x, y, z) are perpendicular to each other.

22. The head-clamping device as claimed in claim 7 in which the axes (x, y, z) are perpendicular to each other.

23. The head-clamping device as claimed in claim 8 in which the axes (x, y, z) are perpendicular to each other.

24. The head-clamping device as claimed in claim 9 in which the axes (x, y, z) are perpendicular to each other.

25. The head-clamping device as claimed in claim 10 in which the axes (x, y, z) are perpendicular to each other.

26. The head-clamping device as claimed in claim 11 in which the axes (x, y, z) are perpendicular to each other.

27. The head-clamping device as claimed in claim 12 in which the axes (x, y, z) are perpendicular to each other.

28. The head-clamping device as claimed in claim 13 in which the axes (x, y, z) are perpendicular to each other.

29. The head-clamping device as claimed in claim 14 in which the axes (x, y, z) are perpendicular to each other.

30. The head-clamping device as claimed claim 15 in which the axes (x, y, z) are perpendicular to each other.

31. The head-clamping device as claimed in claim 16 in which the axes (x, y, z) are perpendicular to each other.

* * * * *